(12) United States Patent
Ettlinger et al.

(10) Patent No.: US 8,945,852 B2
(45) Date of Patent: Feb. 3, 2015

(54) METHOD FOR ELECTROCHEMICAL DETECTION OF BINDING REACTIONS

(75) Inventors: Julia Ettlinger, Gross Kreutz (DE); Nenad Gajovic-Eichelmann, Berlin (DE); Burkhard Micheel, Geswalde (DE); Gudrun Scharte, Berlin (DE); Jörg Schenk, Berlin (DE)

(73) Assignee: Fraunhofer-Gesellschaft zur Förderung der angewandten Forschung e. V. (DE)

( * ) Notice: Subject to any disclaimer, the term of this patent is extended or adjusted under 35 U.S.C. 154(b) by 0 days.

(21) Appl. No.: 13/697,822

(22) PCT Filed: May 25, 2011

(86) PCT No.: PCT/EP2011/002586
§ 371 (c)(1),
(2), (4) Date: Feb. 7, 2013

(87) PCT Pub. No.: WO2011/147563
PCT Pub. Date: Dec. 1, 2011

(65) Prior Publication Data
US 2013/0203065 A1 Aug. 8, 2013

(30) Foreign Application Priority Data
May 25, 2010 (EP) .................... 10005425

(51) Int. Cl.
*G01N 33/542* (2006.01)
*G01N 27/327* (2006.01)
*G01N 33/543* (2006.01)
*G01N 33/74* (2006.01)

(52) U.S. Cl.
CPC .......... *G01N 27/3277* (2013.01); *G01N 33/542* (2013.01); *G01N 33/54306* (2013.01); *G01N 33/5438* (2013.01); *G01N 33/743* (2013.01)
USPC ........................................... 435/7.1; 436/501

(58) Field of Classification Search
CPC ........................ G01N 33/542; G01N 33/54353
See application file for complete search history.

(56) References Cited

U.S. PATENT DOCUMENTS

| | | | |
|---|---|---|---|
| 3,839,153 A | 10/1974 | Schuurs et al. | |
| 4,016,043 A | 4/1977 | Schuurs et al. | |
| 4,960,693 A | 10/1990 | Siddiqi et al. | |
| 6,156,271 A | 12/2000 | May | |
| 2004/0020791 A1* | 2/2004 | Porter et al. | 205/777.5 |
| 2007/0054317 A1 | 3/2007 | Diebold et al. | |
| 2008/0199972 A1 | 8/2008 | Sellrie | |

FOREIGN PATENT DOCUMENTS

| | | |
|---|---|---|
| EP | 0 200 960 | 11/1986 |
| EP | 1 331 482 | 7/2003 |
| WO | 03/062822 | 7/2003 |

OTHER PUBLICATIONS

A.L. Ghindilis et al., "Nanomolar Determination of the Ferrocene Derivatives Using a Recycling Enzyme Electrode. Development of a Redox Label Immunoassay," *Analytical Letters*, vol. 28, No. 1, 1995, pp. 1-11.
R. Sapin et al., "Efficacy of a new blocker against anti-ruthenium antibody interference in the Elecsys free triiodothyronine assay," *Clin Chem Lab Med*, vol. 45, No. 3, 2007, pp. 416-418.
N.J. Forrow et al., "Synthesis, Characterization, and Evaluation of Ferrocene-Theophylline Conjugates for Use in Electrochemical Enzyme Immunoassay," *Bioconjugate Chem.*, vol. 15, No. 1, Jan. 2004, pp. 137-144.
M-Y Wei et al., "Development of redox-labeled electrochemical immunoassay for polycyclic aromatic hydrocarbons with controlled surface modification and catalytic voltammetric detection," *Biosensors and Bioeletronics*, vol. 24, No. 9, 2009, pp. 2909-2914.
I. Coille et al., "Comparison of two fluorescence immunoassay methods for the detection of endocrine disrupting chemicals in water," *Biomolecular Engineering*, vol. 18, 2002, pp. 273-280.
C. Tan et al., "Direct detection of Δ9-tetrahydrocannabinol in saliva using a novel homogeneous competitive immunoassay with fluorescence quenching," *Analytica Chimica Acta*, vol. 658, 2010, pp. 187-192.
S.J. Yoo, et al., "Microfluidic chip-based electrochemical immunoassay for hippuric acid," *Analyst*, vol. 134, 2009, pp. 2462-2467.
R.M. Nielson et al., "Electron Self-Exchange Kinetics for a Water-Soluble Ferrocenium/Ferocene Couple: Rate Modulation via Charge Dependent Calix[6]arene-p-sulfonate Encapsulation," *Inorg. Chem.*, vol. 35, 1996, pp. 1402-1404.
K. Di Gleria et al., "Homogeneous Ferrocene-Mediated Amperometric Immunoassay," *Anal. Chem.*, vol. 58, 1986, pp. 1203-1205.

* cited by examiner

*Primary Examiner* — Shafiqul Haq
*Assistant Examiner* — Carmencita M Belei
(74) *Attorney, Agent, or Firm* — DLA Piper LLP (US)

(57) ABSTRACT

A method for performing homogeneous immunoassay formats with electrochemical detection in solution includes combining two different conjugates as reagents with a sample or a sample/buffer mixture, one conjugate including a redox marker and an analyte molecule and the second conjugate including an anti-redox marker antibody or a specifically binding fragment thereof and a molecule specifically binding the analyte.

14 Claims, 2 Drawing Sheets

A: without progesterone

B: with progesterone

METHOD FOR ELECTROCHEMICAL DETECTION OF BINDING REACTIONS

RELATED APPLICATIONS

This is a §371 of International Application No. PCT/EP2011/002586, with an international filing date of May 25, 2011 (WO 2011/147563 A1, published Dec. 1, 2011), which is based on European Patent Application No. 10005425.3, filed May 25, 2010, the subject matter of which is incorporated herein by reference.

TECHNICAL FIELD

This disclosure relates to a method for direct, high-sensitivity electrochemical detection of antibody-antigen binding reactions and other biochemical interactions in solution, particularly to a method suitable for washing-free and separation-free immunoassays in diagnostics such as automated and microfluidic immunoassays, inexpensive immunoassay systems and test strips for single use.

BACKGROUND

Immunoassays use the antigen-antibody reaction for specific detection of small concentrations of an analyte in complex media such as blood, serum, urine or food. For decades, immunoassays have been indispensable tools in clinical diagnosis, environmental and food analysis for the detection of smallest concentrations of hormones, metabolites, proteins, biomarkers, toxins, pesticides, pathogenic bacteria and viruses. Many of the most important clinical-diagnostic analytes are only inexpensive and quickly measurable with immunoassays as there are no alternative analytical chemical methods offering an equivalent combination of high sensitivity (detection of nanomolar or lower concentrations) and high specificity (detection of the analyte in the presence of interfering substances with a chemically similar structure). Alternative methods such as chromatography (e.g., HPLC, gas chromatography), require an often multi-step sample preparation, e.g., by extraction and chemical derivatization.

Since the invention of the immunoassay 50 years ago by Rosalyn Yalow and Salomon Berson, a plurality of different embodiments have been developed which are designated as different immunoassay formats. The basic distinction between heterogeneous formats such as the ELISA (enzyme-linked immunosorbent assay), and homogeneous formats is made on the basis of the aggregate state of the antibody employed for detection: In the heterogeneous assays, the antibody (more rarely the antigen) is immobilized on a surface (reaction tube, microtiter plate, test strip). All the reaction steps such as washing and separation steps such as the detection likewise take place on the surface. In the homogeneous formats, none of the binding partners is immobilized, no washing and separation steps are necessary, and the detection likewise takes place in solution.

Another possibility to distinguish arises from the detection method used. As it is not possible to make the antibody-antigen binding reaction directly visible, one of the binding partners has to be chemically coupled with a molecular marker or "label" (exception: mass-sensitive biosensors based on surface plasmon resonance, grating couplers, quartz crystal microbalance, surface acoustic waves and similar techniques directly measure the molecular binding reaction in real time if one of the binding partners is immobilized on the sensitive surface. However, these methods are so far only employed in research applications, not in routine analysis). A suitable label has to have a high "specific activity," i.e., it has to produce as many signaling events as possible per label molecule. The most frequently used labels include radioactive isotopes (radioimmunoassay, "RIA"), fluorescent dyes (fluorescein, rhodamines, etc.), fluorescent semiconductor nanoparticles ("quantum dots"), polymer nanoparticles ("latex beads," agglomeration immunoassay), and enzymes, such as peroxidase, together with a colorimetric, fluorogenic or chemiluminescent enzyme substrate (ELISA). Radioactive isotopes possess the highest specific activity, even allowing for the detection of a single label molecule. Due to health hazards emanating from radioactivity, the associated high laboratory requirements ("isotope laboratories") and high cost of the disposal of the residues, radioactivity immunoassays are increasingly replaced by alternative methods such as the ELISA.

Another distinction between different immunoassays results from the type of antibody used. Antibodies are proteins of a complex structure having constant regions which determine the structure and are similarly composed in all the antibody classes and highly variable regions which form the antigen binding sites. The originally used polyclonal sera containing a plurality of antibodies with a variable specificity and affinity are replaced in many applications by monoclonal antibodies which only contain exactly one antibody entity ("clone") with a well-defined specificity and affinity. In theory, monoclonal antibodies may be produced in any amount with identical properties. Furthermore, so-called "antibody fragments" were also used for some analyses which can be produced by enzymatic digestion from whole antibodies. Single-chain antibodies are recombinant antibody fragments which can be produced by genetic engineering methods. In principle, all types of antibodies and molecular binders derived therefrom may be used in the known immunoassay formats.

The best known clinical analytes that can be detected with immunoassays include hCG (pregnancy test), thyroid hormones, such as TSH (thyroid disorders), steroid hormones (endocrinology, fertility) and PSA (biomarker for prostate carcinoma).

In summary, it can be said that immunoassays based on monoclonal antibodies or polyclonal antisera are among the most important analytical chemical methods of biotechnology, clinical diagnosis, environmental and food analysis and have a high commercial value.

A plurality of methods to perform an immunoassay is described in the prior art. Most heterogeneous immunoassays require several manual processes such as, e.g., pipetting steps, sample dilution and washing steps which have to follow an exact time protocol. Thus, trained personnel and a laboratory specifically equipped for these processes are typically required to correctly perform such assays. The required detection devices ("ELISA reader," microtiter plate reader, immunoassay analyzer) are expensive and not portable. Protocols to perform an ELISA test are described in U.S. Pat. No. 4,016,043A and U.S. Pat. No. 3,839,153A, for example. Those skilled in the art easily recognize that such complex analytical processes can only be performed by trained personnel and only in a suitable laboratory environment. Automation of such processes is very laborious and requires highly complex automatons.

The heterogeneous lateral-flow immunoassay format ("test strip" immunoassay) has become accepted for on-site use. U.S. Pat. No. 6,156,271A describes a modern variant of this assay format. That test runs by itself after addition of the sample solution and detection is effected on a purely visual basis (reading of the presence of one or two colored bands on the test strip by the user). It is obvious that such a reading method cannot result in quantitative results (i.e., precise measurements of concentrations), but only a yes/no statement or a semiquantitative statement (concentration is below/above a certain threshold) is possible.

It is known that in contrast, homogeneous immunoassays are particularly suited to realize fast, quantitative and fully automated immunoassays. In homogeneous immunoassays, the signal generation is carried out simultaneously with the binding reaction. Unlike the above-described heterogeneous immunoassays, homogeneous immunoassays mostly consist of only one or a few dosing operations, an incubation time and a detection step. In the ideal case, only the mixing of the sample and a ready-made reagent mixture is required before a final value can be measured (so-called "mix and measure" test). In the case of a 1:1 mixture, i.e., identical volume fractions of sample and reagent mixture, dosing is possible with the simplest of means and with high precision.

It can be easily seen that a homogeneous immunoassay also allows for the shortest possible analysis duration as the measurement is possible immediately after achieving the binding equilibrium between antibody and antigen.

A disadvantage of homogeneous immunoassays is that higher chemical synthesis expenditure is required to couple the binding reaction with the signal generation.

In U.S. Pat. No. 4,960,693A, synthesis of an antibody-enzyme fragment 1 conjugate is described such that the functional enzyme ("holoenzyme") is only formed after binding of the antigenenzyme fragment 2 conjugate. Chemical synthesis of such conjugates is sterically challenging and not equally well-suited for all types of analytes. Furthermore, additional reaction time is required due to the coupling with the enzyme reaction which is why that principle was not accepted.

A more universal and chemically easier approach for low molecular analytes is the fluorescence polarization immunoassay such as described in, e.g., EP0200960A. In that process, a conjugate of the analyte (estriol) and a fluorescent dye, in most cases fluorescein, was synthesized. The measured solution was illuminated with linearly polarized excitation light. The emitted fluorescent light was not polarized (depolarized) as long as the conjugate was freely in solution. Only after binding to the antibody, the rotation velocity of the conjugate was limited to such an extent that the emitted fluorescent light was also polarized. Through this, the binding equilibrium was measured in real time. The disadvantage of that method is the high expenditure in terms of equipment for detection as a polarized monochromatic light source and two fluorescence detectors equipped with polarizing filters are required for detection. Therefore, that principle was only accepted in special laboratory applications, but not in routine diagnosis and for on-site use. Additionally, it is only suited for low-molecular analytes. An additional method is required for protein analytes.

A technically easier detection of low-molecular analytes was realized in the method of Sellrie et al., using a europium cryptate immunoassay (abbr.: EuCr) as an example (US2008199972A). In that case, an EuCr-fluorescein conjugate is synthesized wherein a linker as short as possible consisting of one to no more than three methylene groups may be present between the EuCr and the fluorescein. Besides the anti-EuCr antibody, an anti-fluorescein antibody which, after binding to fluorescein, quenches the latter's fluorescence is additionally employed. The signal generation principle is based on the fact that for sterical reasons, only one of the two antibodies can bind the conjugate. The binding equilibrium and thus the fluorescence intensity depends on the concentration of free EuCr and can be measured directly in real time. An advantage of that system is that only one conventional fluorescence detector is required. The disadvantage is that it is likewise only suited for low-molecular analytes and the conjugate synthesis is chemically challenging.

An alternative homogeneous immunoassay method for low-molecular analytes likewise based on the principle of the binding-dependent fluorescence quenching was published by Coille et al. and in modified form by Tan et al. (I. Coille, S. Reder, S. Bucher and G. Gauglitz, Biomol. Eng 18 (2002), 273-280; Chongxiao Tan, Nenad Gajovic-Eichelmann, Walter F. M. Stocklein, Rainer Polzius, Frank F. Bier, Analytica Chimica Acta 658 (2010), 187-192). In that case, the analyte, tetrahydrocannabinol, is coupled to a protein, bovine serum albumin, which additionally carries several fluorescence quencher molecules on the surface. The anti-tetrahydro-cannabinol antibody is conjugated with a fluorescence molecule. The fluorescence is quenched when the antibody binds to the conjugate. If the analysis sample contains free tetrahydrocannabinol, the antibody binds the latter and fluoresces again. The advantage of that method is that, as with Sellrie et al., the simple measuring setup can be used for fluorescence measurement. Again, the chemically challenging synthesis of the analyte-quencher conjugate and the antibody-fluorophore conjugate is disadvantageous in that case.

Although the fluorescence measurement technique is very often employed in the biosciences, it is an elaborate and thus expensive measurement technique. Inexpensive and compact detectors, e.g., for on-site use, are rather realized with other detection methods. Electrochemical detection methods make the technically simplest and most strongly integrated measuring devices possible and have achieved acceptance, e.g., in the field of disposable biosensors for glucose over all the optical measuring methods. Therefore, efforts have been made for many years to realize homogeneous immunoassays based on a simple electrochemical detection principle.

A prerequisite for a homogeneous immunoassay with electrochemical detection is the availability of a sensitive electroanalytical method and a redox-active label/marker having high specific activity. Amperometric and voltammetric methods are sensitive and suitable methods. The specific activity of the redox label/marker mainly depends on the velocity constant of the heterogeneous electron transfer with the electrode and of the detection potential. Those skilled in the art have reached the consensus that a detection potential in the range of from −200 mV to +200 mV (against a silver/silver chloride reference electrode, in the following abbreviated with vs. Ag/AgCl) is ideal for measurements in biological solutions such as blood. The electron transfer constant is a function of the chemical structure of the redox label/marker as well as the diffusion coefficient and the electrode material used. A plurality of redox mediators are known which possess beneficial electrochemical properties and thus are in principle suitable labels/markers for an immunoassay. For use in biological media, the redox mediators must not react with sample constituents and have to be stable in an oxidized and reduced state and be sufficiently water-soluble. These include, e.g., the organic molecules such as hydroquinone/quinone, p-aminophenol, organic/inorganic sandwich molecules such as ferrocene, and inorganic complexes such as, e.g., hexacyanoferrate(II/III) or bis-bipyridine osmium. The water solubility of ferrocene and bis-bipyridine osmium is poor such that in most cases water-soluble derivatives are employed in this connection.

US2007/054317 describes water-soluble osmium-based redox molecules having the above-mentioned beneficial properties and different electrochemical immunoassay formats and electrode geometries, e.g., interdigital electrodes, by which the mentioned water-soluble redox molecules can be detected in a sensitive manner. Apart from the use of new redox mediators and of antibody and antigen conjugates based on the latter, the assay formats described in US2007/054317 do not surpass the prior art. In particular, no new, highly sensitive homogeneous immunoassay format is described.

EP1331482A1 describes an electrochemical immunoassay method wherein conjugates of ferrocene and other redox mediators with the analyte are employed. An enzyme biosensor, e.g., a glucose sensor, is used for detection, the release of the ferrocene-analyte conjugate leading to a modulation of the electrochemical signal of the glucose sensor. A disadvantage of the described coupling chemistry is that a protein such as human serum albumin, is used to produce a well water-soluble conjugate. It is known that it is not possible to synthesize protein-redox mediator conjugates with a precisely defined stoichiometric ratio. The characteristic of the test is thus always different from one batch to another. Those skilled in the art are also aware of the fact that such an indirect signaling method entails a danger that inhibitors from the enzyme reaction can modulate the enzyme reaction just like the redox mediator-analyte conjugate. A method in which the redox mediator conjugate directly modulates the electrochemical signal would be more robust.

The homogeneous electrochemical assay for hippuric acid in a microfluidic chip by Sung et al. is designed in accordance with such a principle (Sung Ju Yoo, Young Bong Choi, Jong Il Ju, Gun-Sik Tae, Hyug Han Kim and Sang-Hoon Lee. Analyst 134 (2009), 2462-2467). A ferrocene-hippuric acid conjugate is synthesized and an anti-hippuric acid antibody is used. The conjugate and the antibody bound to polymer particles are added to the sample in a precisely defined amount. If a sample contains no free hippuric acid, the conjugate binds to the antibody-loaded particles and is centrifuged with the latter. In a voltammetric experiment, a correspondingly small current will flow in the supernatant at the oxidation potential of the ferrocene. However, if the sample contains free hippuric acid, the particle-bound antibody preferably binds to the latter, the conjugate remains in solution during centrifugation and a correspondingly higher current will flow in the voltammetric experiment (at the oxidation potential of the ferrocene). That assay and all the assays following this principle have severe disadvantages which practically do not allow for a use in diagnostics.

First, the oxidation potential of ferrocene (+400 mV vs. Ag/AgCl) is too high for the selective detection in blood and blood serum. Second, a centrifugation step is not acceptable for most on-site applications. Third, despite the separation step (centrifugation), that method is very insensitive. For example, Sung et al. measured ca. 10 mg/mL of hippuric acid as the lowest concentration. That equals a concentration of 55 mM. However, typical immunoassay analytes have to be measured in the nanomolar concentration range (or lower), i.e., a million times more sensitive.

A homogeneous electrochemical assay which does without a separation step was presented by Di Gleria et al. (Katalin Di Gleria, H. Allen, O. Hill, Calum J. McNeil, Anal. Chem. 1988, 58, 1203-1205). A conjugate of ferrocene and the analyte, lidocain, as well as the anti-analyte antibody are also added to the sample in that case. As the detection principle, an enzyme reaction is used for which the ferrocenium-antigen conjugate is acting as a redox mediator. If the sample contains no free analyte, the conjugate binds to the antibody and the enzyme reaction, here glucose oxidase, is delayed and the amperometric current becomes smaller. A disadvantage of that format is that it is not sensitive enough for a typical immunoassay. For example, a lower detection limit of ca. 5 µM was achieved in serum, ca. 1000 times higher than in typical immunoassays.

A variant of that homogeneous redox immunoassay was described in which the redox mediator conjugate is directly electrochemically measured. In that case as well, only insufficient detection limits were achieved.

The assay and all the assays following a similar principle (i.e., the modulation of the diffusion constant through the antibody binding) have severe disadvantages which complicate use in diagnostics. The main disadvantage is low sensitivity as modulation of the diffusion constant only entails a slight signal modulation: even if the redox-active conjugate is completely bound by the antibody, an appreciable amperometric or voltammetric signal can still be measured. It would be desirable if the antibody-bound conjugate would produce no electrochemical signal at all.

The same applies to the principle of the modulation of an enzyme reaction through depletion of the redox mediator after binding to an antibody. That format could also only detect micromolar concentrations (or higher).

In summary, it can be said that homogeneous electrochemical immunoassays based on modulation of the diffusion constant of a low-molecular conjugate or modulation of an enzyme reaction through depletion of the redox mediator after binding to an antibody are not sufficiently sensitive to measure concentrations in the nanomolar range (or lower) as are typical for immunoassay analytes. Therefore, despite the inexpensive detection system, none of these assays can be used in a noteworthy commercial application.

Against this background, it could be helpful to provide a new improved method for performing an immunoassay in solution which no longer has the mentioned disadvantages and in particular offers a markedly improved sensitivity.

SUMMARY

We provide a method for performing homogeneous immunoassay formats with electrochemical detection in solution including combining two different conjugates as reagents with a sample or a sample/buffer mixture, one conjugate including a redox marker and an analyte molecule and the second conjugate including an anti-redox marker antibody or a specifically binding fragment thereof and a molecule specifically binding the analyte.

We also provide a redox marker antibody or a fragment thereof which specifically binds to a redox marker, selected from the group consisting of ferrocene and ferrocene derivatives, bis-bipyridyl osmium complexes, osmium-based complexes, bipyridyl ruthenium complexes, ruthenium-based complexes, p-aminophenol, hexacyanoferrate (II/III), quinones, redox markers suitable for electrochemical immunoassays, and which inhibits redox activity of the redox marker bound thereto to an extent of more than 90%.

We further provide a bispecific antibody conjugate that performs the method for performing homogeneous immunoassay formats with electrochemical detection in solution including combining two different conjugates as reagents with a sample or a sample/buffer mixture, one conjugate including a redox marker and an analyte molecule and the second conjugate including an anti-redox marker antibody or a specifically binding fragment thereof and a molecule specifically binding the analyte, including a redox marker antibody or a fragment thereof which specifically binds to a redox marker, selected from the group consisting of ferrocene and ferrocene derivatives, bis-bipyridyl osmium complexes, osmium-based complexes, bipryidyl ruthenium complexes, ruthenium-based complexes, p-aminophenol, hexacyanoferrate (II/III), quinones, redox markers suitable for electrochemical immunoassays, and which inhibits redox activity of the redox marker bound thereto to an extent of more than 90% and an anti-analyte antibody or a fragment thereof.

DETAILED DESCRIPTION

The method for performing homogeneous immunoassay formats with electrochemical detection is characterized in that two different conjugates as reagents are combined with the sample or the sample/buffer mixture, one conjugate comprising a redox marker and an analyte molecule and the second conjugate comprising an anti-redox marker antibody or a specifically binding fragment thereof and a molecule specifically binding the analyte.

The analyte can generally be any molecule detectable in an immunoassay or another binding assay, a specific binding partner existing for the molecule. The analyte can be low molecular, i.e., having a molecular weight of ≤ about 1000 daltons, or be higher or high molecular. Examples of higher and high molecular weight analytes are nucleic acids, peptides and proteins. Particularly preferred analytes are low molecular weight organic molecules and proteins/peptides, e.g., hormones, enzymes, biomarkers, biologic active and hazardous substances and other physiologically or metabolically relevant substances.

The molecule specifically binding the analyte can be an anti-analyte antibody or a fragment thereof, an aptamer, a peptide, a nucleic acid or a typically organic chelator which specifically binds the analyte (e.g., in a special binding pocket or coordination structure) and is not an antibody (also referred to in literature as a "host molecule" for a "guest molecule"). It is preferably an anti-analyte antibody or a fragment thereof.

More specifically, the method is characterized in that the presence of free analyte in the sample induces or promotes binding of the redox marker to the anti-redox marker antibody or the specifically binding fragment thereof, the redox activity of the bound redox marker being inhibited ("quenched") by this binding whereby a detectable signal is generated or changed. The method is or includes typically a competitive assay.

For example, a suitable method design is as follows: a bispecific antibody conjugate, comprising an anti-analyte antibody and an anti-redox marker antibody, and the redox marker-analyte conjugate are dissolved in a buffer. Part of the conjugate molecules binds to the bispecific antibody conjugate, the majority of them binding to the anti-analyte end of the bispecific antibody conjugate as the anti-analyte antibody, in particular under the steric conditions of the conjugate, preferably has a markedly higher affinity constant than that of the anti-redox marker antibody. The redox marker end of the conjugate is thus practically not bound and therefore freely accessible for the electrochemical measurement (e.g., amperometry or voltammetry) and a high reduction current is measured. If free analyte molecules from the sample now come into play, they displace the analyte end of the analyte-redox marker conjugate from the binding sites of the analyte antibody. The redox marker ends of the conjugate can only now bind to the anti-redox marker antibody part of the bispecific antibody conjugate whereby the redox activity of the bound redox marker is inhibited ("quenched"), and a reduced electrochemical signal is measured.

The method surpasses the prior art by far as it transfers the principle of "quenching" a signal through the antibody-antigen binding (analogous to fluorescence quenching) to direct electrochemical detection for the first time. Fluorescence quenching immunoassays belong to the most sensitive and quickest homogeneous immunoassays as the signal is generated in real time proportionally to the antibody-antigen binding. Such a signal characteristic is now also realized in an electrochemical detection for the first time.

Ferrocene (or any derivatives of ferrocene), bis-bipyridyl osmium complexes and other osmium-based complexes, bipyridyl ruthenium complexes and other ruthenium-based complexes, p-aminophenol, hexacyanoferrate(II/III), hydroquinones/quinones or other redox mediators, in particular other redox markers known and suitable for immunoassays, can be used as redox-active markers (analogous to the fluorophore). The "quenching" of the redox activity of the ferrocene or another redox mediator under conditions of an immunoassay was not possible in the prior art. It was indeed described in papers such as that by Nielson et al. (Roger M. Nielson, Joseph T. Hupp, Inorg. Chem. 1996, 35, 1402-1404), that calixarenes which form a weak bond to ferrocene are able to completely quench the redox activity of ferrocenes, but only in concentrations of ca. 10 mM and higher. Such high concentrations of a redox quencher are totally unsuitable for immunoassays.

We surprisingly found that monoclonal antibodies which were generated for binding ferrocene have such a quenching characteristic. A particularly effective new monoclonal antibody exclusively binds the oxidized form of ferrocene, the ferrocenium cation (or ferricinium), in the following referred to as ferrocenium. The redox activity of the bound ferrocenium is completely quenched through this. In the bound state, it can no longer be reduced on an electrode (glass-carbon, noble metal). In the examples of the method, the ferrocenium-binding antibody is used as a redox quencher (analogous to the fluorescence quencher).

However, any other antibody which binds the redox mediator used in the test and thus inhibits (quenches) its redox activity can also be employed. In this connection, it is irrelevant if the antibody binds the oxidized or reduced state of the redox mediator. However, an antibody binding the oxidized mediator offers particular advantages in some applications such as in the case of the anti-ferrocenium antibody used in the method for the first time. The reason for this is the lower detection potential which can be used for reduction of the redox marker (in the application example, detection is carried out at +100 mV vs. Ag/AgCl. In the case of an oxidation, detection would have to take place at +250 to +400 mV which would lead to increased unspecific signals in the blood serum).

These redox marker antibodies having a quencher effect and bispecific antibody conjugates comprising these represent one of the aspects of our method. The redox marker antibodies having a quencher effect are able to inhibit (to "quench") the redox activity of the bound redox marker to a large extent, preferably to more than 80%, more preferably to more than 90%, yet more preferably to more than 95% or completely.

The term "antibody" shall generally also comprise specifically binding fragments thereof, unless something else can expressly be understood from the context.

With an anti-ferrocenium antibody described herein for the first time, a competitive immunoassay for detection of ferrocenium (or ferrocene) can be realized which, however, would not be of any great technical importance. The method only has a high technical benefit and a high commercial value when any analytes can be detected through this by the electrochemical immunoassay. To this effect, formation of a ferrocenium-anti-ferrocenium immunocomplex has to be coupled with any monoclonal antibody such that binding the target analyte to the complementary antibody leads to modulation of the ferrocenium-anti-ferrocenium bond. The elegant approach of coupling two immunoreactions via a conjugate of both antigens connected with a very short linker such that in each case only the anti-pesticide antibody or the anti-fluorescein antibody can bind, described by Sellrie et al. (US2008199972A), could not be used in the case of our method as ferrocene conjugates coupled with low-molecular substances are typically not water-soluble. For practical use, a ferrocene-analyte conjugate having a sufficiently high water solubility had to be prepared. A number of water-soluble linker molecules which can be used for the synthesis of bioconjugates is known. Due to good water solubility, the marginal unspecific binding to proteins and surfaces and availability of a plurality of chain lengths and chemical functions, polyethylene glycol linkers (synonym: polyethylene oxide linker, PEG, PEO) belong to the most frequently used water-soluble linkers. Polyethylene glycol linkers (synonym: polyethylene oxide linkers) are linear molecules which may have coupleable functions on one or both ends, e.g., carboxyl groups, amino groups, thiol groups and the like. Water solubility of polyethylene glycol linkers is very high and increases with increasing chain length of the linker.

To prepare the conjugates used in the method, a bifunctional water-soluble linker of sufficient chain length, e.g., a 400-30,000 Da PEG linker with two terminal coupleable functions, preferably a 2000 Da diamino-PEG linker, is used to couple ferrocene or another suitable redox mediator to one end and the target analyte to the other end. By using PEG linkers of sufficient length, analytes not soluble in water can also be made accessible for the test. Homobifunctional linkers having the same coupling function on both ends can be used as can be heterobifunctional linkers having two different coupling functions.

We discovered that, with the ferrocene-analyte conjugate in the presence of the free anti-ferrocenium antibody, the free anti-analyte antibody and the ferrocene-analyte conjugate, no sufficient modulation of the ferrocene signal by the analyte took place. We also discovered that the ferrocenium-analyte conjugate had to be kept in the oxidized state for the entire duration of the analysis to achieve measurable signals. We surprisingly discovered that in some acidic buffers, ferrocene constantly remains in the oxidized state. In our method, the assay is preferably performed at pH values of pH 1 to pH 7, particularly preferably pH 4 to pH 5. Suitable buffer salts are, e.g., phosphate, MES, HEPES, TRIS, Bistris, acetate, glycylglycine, glycine.

A surprisingly simple, new principle to couple the ferrocenium-anti-ferrocenium binding reaction with the analyte-anti-analyte binding reaction was now discovered. To this effect, a bispecific antibody conjugate was prepared by coupling the anti-ferrocenium antibody in a stoichiometric ratio (1:1) with the anti-analyte antibody in which a short linker having a length of no more than 10 methylene moieties was used. Through this, the above-described, desired signal quenching characteristic could be achieved in an electrochemical immunoassay for the first time.

Figure 1:
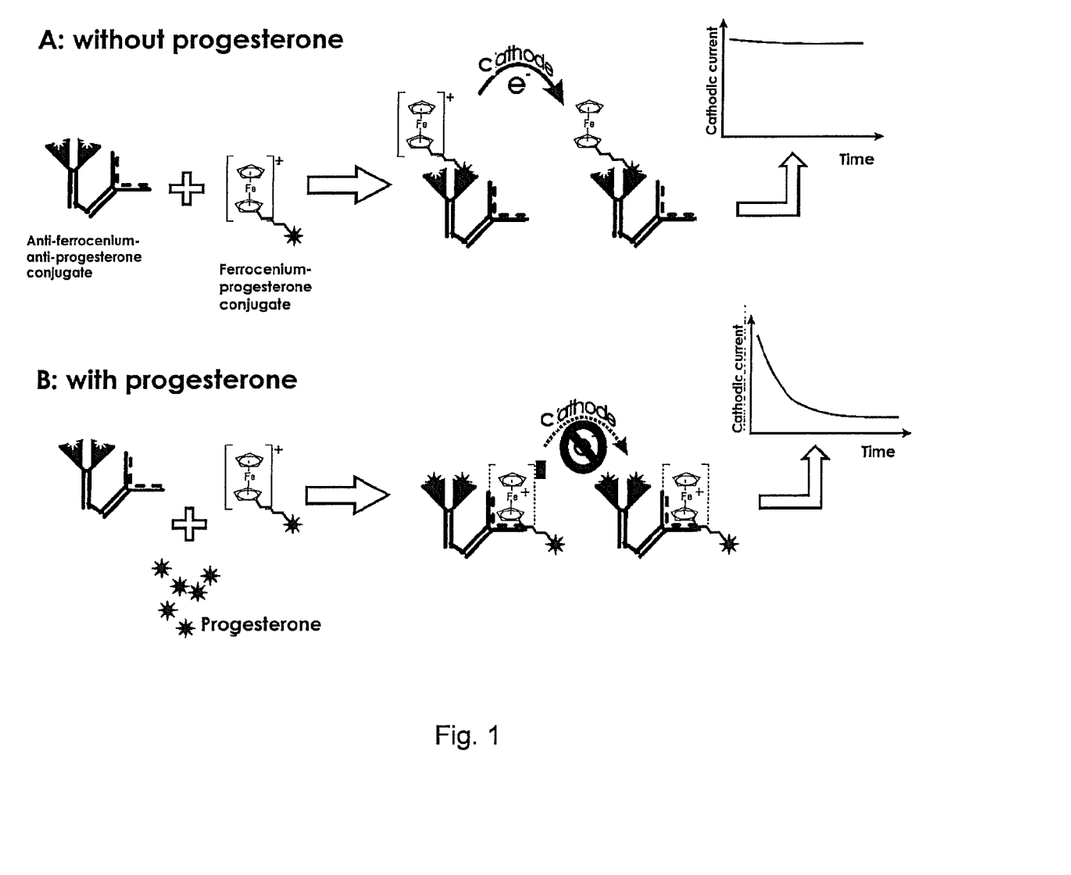
FIG. 1 is a schematic representation of the immunoassay in an example of progesterone detection.

In this connection, the function principle, explained in an example of a competitive progesterone immunoassay, is as follows: the bispecific antibody conjugate consisting of an anti-progesterone antibody and an anti-ferrocenium antibody, and the ferrocenium-progesterone conjugate are dissolved in a buffer. Part of the conjugate molecules binds to the bispecific antibody conjugate, the majority of them binding to the anti-progesterone end of the bispecific antibody conjugate (as the antibody has a higher affinity constant). The ferrocenium end of the conjugate is practically not bound as the PEG linker is too short for this, and would also have to adopt an energetically unfavorable, bent conformation. The ferrocenium end is therefore freely accessible for the electrochemical measurement (amperometry or voltammetry) and a high reduction current is measured. If free progesterone molecules from the sample now come into play, these displace the progesterone end of the progesterone-ferrocenium conjugate from the binding sites of the progesterone antibody. The ferrocenium ends of the conjugate can only now bind to the anti-ferrocenium antibody part of the bispecific antibody conjugate, and a reduced electrochemical signal is measured (see FIG. 1).

Figure 2:
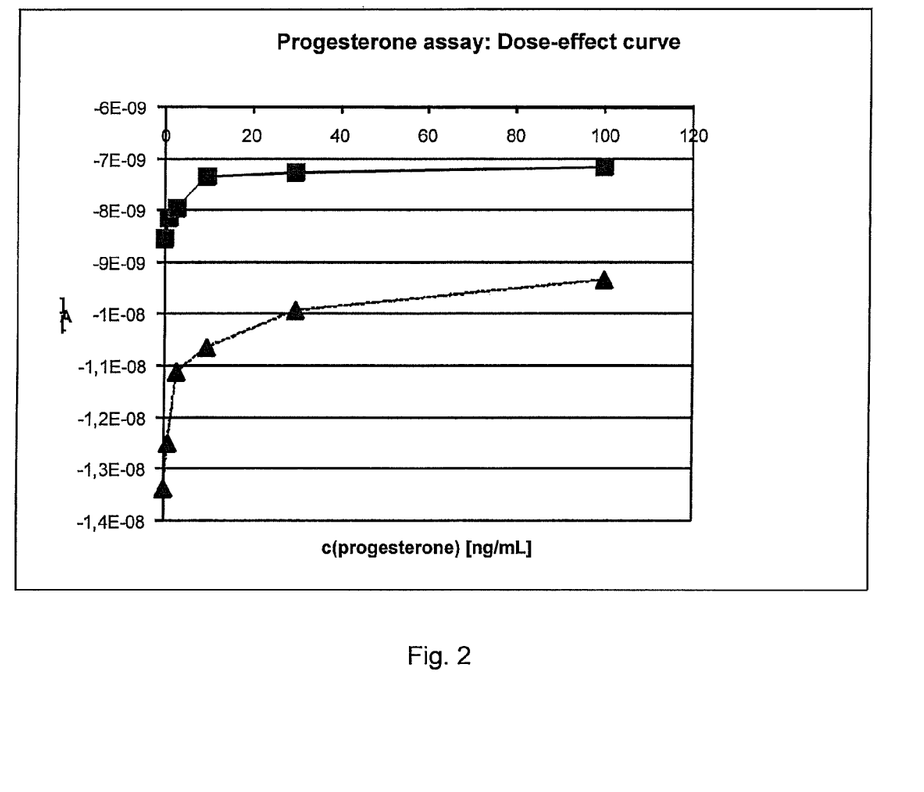
FIG. 2 is a dose-effect curve for the amperometric measurement of progesterone in accordance with the method.

When adding an excess of bispecific antibody conjugate in comparison to the ferrocenium-analyte conjugate, most of the ferrocenium residues are bound by the antibody conjugate and the electrochemical signal is reduced to almost zero, thus quenched. However, it is known that the antibody concentration or concentration of the bispecific antibody in the immunoassay is chosen such that a maximum sensitivity for progesterone results such that the antibody conjugate is added in a deficient amount in a highly sensitive assay. In this case, the electrochemical (total) signal is not completely quenched, even with a high progesterone concentration. We thus discovered that a progesterone assay is most sensitive when the electrochemical signal can only be quenched by ca. 50% by means of progesterone addition (see FIG. 2).

The achieved signal quenching characteristic had not yet been achieved in electrochemical immunoassays as no corresponding quencher molecules were available.

The anti-ferrocenium antibodies are an example of such a redox quencher molecule. However, it is likewise possible to prepare analogous antibodies binding other redox markers and quenching their signals. The use of such antibodies in a bispecific antibody conjugate is also part of this disclosure.

We provide a method for performing direct, homogeneous immunoassays in solution with sensitive electrochemical detection which is characterized in that nanomolar concentrations of low-molecular or high-molecular analytes can be measured, that none of the reagents is immobilized, no separation and washing steps take place and the binding reaction is detected electrochemically in real time.

The technical application of the method is particularly easy as it can be employed with different electroanalytical techniques which are known, does not require modifications of the measuring electrode (e.g., chemical modification, membranes, coating with thin films, lateral structuring or the like) and is virtually scalable in any manner (reduction of the electrode dimensions, reduction of the analysis volume). As the signal generation principle, i.e., the quenching of the redox activity of any redox mediator, can be applied to all the known electroanalytical measurement techniques such as, e.g., amperometry, voltammetry, coulometry, amperometric titration, coulometric titration, potentiometry, impedance spectroscopy and the like, the method can be combined with all those methods to create new immunoassay applications. For example, amperometry can be the method of choice in some cases, e.g., to achieve a total system as inexpensive as possible or to employ existing amperometric detectors (e.g., glucose-biosensor measuring devices) for the use of immunoassays. Depending on the particular application and the desired analyte, it is possible to vary the electroanalysis technique without in principle having to develop the immunoassay anew.

The variability and technical applicability of the new immunoassay is particularly clearly shown when it is employed in microfluidic analysis systems (lab-on-a-chip systems). This is particularly easily possible as it is a homogeneous immunoassay without immobilized components and without separation steps. The reagents can be introduced into the lab-on-a-chip system in liquid or dried form such that they are released by addition of the sample and the assay is started. The measurement signal can be measured continuously or only at the beginning and the end of the analysis (after achieving the binding equilibrium). No synchronization of processes, dosing and washing or centrifugation steps is necessary to obtain the analysis result. In contrast to many optical measurement methods (e.g., photometry, fluorescence measurement), the signal-to-noise ratio for electroanalytical methods does not deteriorate, even in the case of miniaturization, i.e., no new and elaborate detectors and amplifiers have to be developed for miniaturized electrodes.

The high value of our method is also demonstrated by the fact that it is possible with this method to realize highly sensitive disposable immunosensors for single use such as, e.g., in the pregnancy test customary nowadays in accordance with the lateral flow immunoassay principle. The electronics required for detection (e.g., an amperometric circuit) can be integrated in an inexpensive portable device (e.g., a measuring device for glucose test strips) or can even be realized as disposable electronics (e.g., a printed circuit or a highly integrated circuit).

The method is likewise also suited for laboratory analyzers fully automatically performing a number of different immunoassays in parallel. In this case, the short analysis time of the method of 1 to 5 minutes has a significant effect.

In a specific example of the method, the required reagents are added in soluble form and an electrochemical detection of the binding event is carried out in real time.

In another specific example, all the required reagents are added to the sample as a ready-made mixture and an electrochemical detection of the binding event is carried out in real time (mix-and-measure principle).

In yet another specific example, all the required reagents are provided as dry reagents in a suitable reaction vessel (e.g., Eppendorf tube, microtiter plate, lab-on-a-chip system, test strip) and only dissolved by addition of the sample and, optionally, a buffer which marks the beginning of the analysis.

In still another, particularly beneficial specific example, the immunoassay is performed in a microfluidic analysis system (lab-on-a-chip).

In a typical example, the immunoassay is performed on a fully automated analyzer.

Another alternative of the method can be achieved by using a structured electrode, e.g., an interdigital electrode, instead of a simple electrode for detection, by which sensitivity of the analysis can be further increased via the so-called "redox recycling."

Another advantageous modification of the method is that an enzymatically catalyzed cyclic reaction (e.g., electrochemical reduction, followed by enzymatic reoxidation of ferrocenium) is employed instead of a simple electrochemical redox reaction (e.g., reduction of the ferrocenium to ferrocene), a so-called "enzyme recycling," by which sensitivity of the analysis can be further increased.

The method is particularly suited for measurements within the low nanomolar concentration range and is ca. 1000 times more sensitive than known homogeneous electrochemical immunoassays without separation steps. This enormous improvement of the sensitivity is achieved by the above-described new signaling principle in which the redox activity of the redox-active conjugate can be completely quenched after binding to the antibody (instead of only reducing the diffusion constant as in known methods).

In this connection, the electrochemical measurement method is technically as simple as in the above-mentioned methods as a simple amperometric or voltammetric measurement on conventional, uncoated electrodes (e.g., glass-carbon electrodes) is carried out. The manual handling steps are limited to addition of the reagents as well as addition of the sample solution. A separation step is not necessary. The method also allows for an analysis in accordance with the mix-and-measure principle and is particularly suited for automation. In this connection, the method is well scalable, i.e., to miniaturized volumes, e.g., applicable in microfluidic applications (lab-on-a-chip). Because of this characteristic and the low detection potential of typically +100 mV (vs. Ag/AgCl), the method is thus suitable for direct measurement of low-molecular analytes such as, e.g., steroid hormones, as well as of high-molecular analytes such as, e.g., hCG, or protein markers in complex biological samples such as, e.g., blood.

The method is thus suited for a plurality of commercially important immunoassays and is able to replace existing detection methods which are technically elaborate (and thus expensive) or can only with difficulty be miniaturized and be automated. It is suited for applications in clinical diagnosis, environmental and food analysis and is due to the good suitability for miniaturization and technical simplicity particularly suited for applications outside of the laboratory (on-site applications, point-of-care analyses, disposable sensors, lab-on-a-chip immunoassay). The method thus has the potential to replace conventional, expensive detection systems such, as e.g., fluorescence detectors or fluorescence polarization detectors, in many applications.

The following non-limiting examples will explain the method in more detail.

EXAMPLE 1

Direct Competitive Progesterone Immunoassay in Blood Serum

Devices: Electrochemical Stirred Cell, Operating Volume of 1 mL, potentiostat in amperometric mode
Buffer: acetate buffer, pH 4.4
Sample: human serum, undiluted,
Calibrator: human serum, undiluted, mixed with 2 ng/mL, 4 ng/mL, 10 ng/mL, 20 ng/mL, 100 ng/mL, 200 ng/mL of progesterone
Method steps:
  Filling of the electrochemical measurement cell with 450 µL of acetate buffer, pH 4.4
  Polarization of the working electrode to +100 mV (vs. Ag/AgCl)
  Addition of 10 µL of bispecific antibody conjugate (final concentration ca. 0.1 µg/mL)
  Addition of 10 µL of redox marker-progesterone conjugate (final concentration ca. 100 nM)
  Addition of 30 µL $H_2O_2$/peroxidase (final concentration 5 mM $H_2O_2$, peroxidase 0.02 nM)

Measurement of the basic signal

Addition of 500 µL of human serum (or 500 µL of calibrator)

Measurement of the final signal 180 sec after the serum addition

The evaluation is performed on the basis of a previously measured dose-effect curve or on the basis of a 2-point calibration.

EXAMPLE 2

Direct Competitive Progesterone Immunoassay in Saliva

Devices: electrochemical stirred cell, operating volume of 1 mL, potentiostat in amperometric mode
Buffer: acetate buffer, pH 4.4
Sample: human saliva, 1:5 dilution,
Calibrator: human saliva, 1:5 dilution, mixed with 2 ng/mL, 4 ng/mL, 10 ng/mL, 20 ng/mL, 100 ng/mL, 200 ng/mL of progesterone
Method steps:
Filling of the electrochemical measurement cell with 450 µL of acetate buffer, pH 4.4

Polarization of the working electrode to +100 mV (vs. Ag/AgCl)

Addition of 10 µL of bispecific antibody conjugate (final concentration ca. 0.1 µg/mL)

Addition of 10 µL of redox marker-progesterone conjugate (final concentration ca. 100 nM)

Addition of 30 µL $H_2O_2$/peroxidase (final concentration 5 mM $H_2O_2$, peroxidase 0.02 nM)

Measurement of the basic signal

Addition of 500 µL of human saliva, 1:5 dilution (or 500 µL of calibrator)

Measurement of the final signal 180 sec after the addition of saliva

The evaluation is performed on the basis of a previously measured dose-effect curve or on the basis of a 2-point calibration.

EXAMPLE 3

Direct Competitive Human Chorionic Gonadotropin Immunoassay (hCG) in Urine

Devices: electrochemical stirred cell, operating volume of 1 mL, potentiostat in amperometric mode
Buffer: acetate buffer, pH 4.4
Sample: human serum, undiluted,
Calibrator: human serum, undiluted, mixed with 10 mIU/mL, 20 mIU/mL, 40 mIU/mL, 100 mIU/mL, 200 mIU/mL of hCG
Method steps:
Filling of the electrochemical measurement cell with 450 µL of acetate buffer, pH 4.4

Polarization of the working electrode to +100 mV (vs. Ag/AgCl)

Addition of 10 µL of bispecific antibody conjugate (final concentration ca. 0.3 µg/mL)

Addition of 10 µL of redox marker-hCG conjugate (final concentration ca. 200 nM)

Addition of 30 µL $H_2O_2$/peroxidase (final concentration 5 mM $H_2O_2$, peroxidase 0.02 nM)

Measurement of the basic signal

Addition of 500 µL of human serum (or 500 µL of calibrator)

Measurement of the final signal 180 sec after the serum addition

The evaluation is performed on the basis of a previously measured dose-effect curve or on the basis of a 2-point calibration.

The invention claimed is:

1. A method for performing homogeneous immunoassay formats with electrochemical detection in solution for the detection of an analyte in a sample comprising:
   (a) combining a water-soluble first conjugate and a second conjugate as reagents with the sample or the sample in a buffer solution, the first conjugate comprising a redox marker and the analyte conjugated via a linker and the second conjugate comprising an anti-redox marker antibody or a fragment that binds the redox marker and a molecule specifically binding the analyte conjugated via a linker,
   (b) binding the first conjugate and the second conjugate, whereby a detectable signal is generated or changed, and
   (c) detecting the signal;
wherein an affinity constant of the molecule specifically binding the analyte is greater than an affinity constant of the anti-redox marker antibody or fragment that binds the redox marker.

2. The method according to claim 1, wherein presence of free analyte in the sample induces or promotes binding of the redox marker to the anti-redox marker antibody, redox activity of the bound redox marker being inhibited by such binding, whereby a detectable signal is generated or changed.

3. The method according to claim 1, wherein the redox marker is selected from the group consisting of ferrocene and ferrocene derivatives, bis-bipyridyl osmium complexes and osmium-based complexes, bipyridyl ruthenium complexes and ruthenium-based complexes, p-aminophenol, hexacyanoferrate(II/III), quinones and redox markers known for electrochemical immunoassays.

4. The method according to claim 3, wherein the redox marker is ferrocenium and the anti-redox marker antibody is a monoclonal anti-ferrocenium antibody.

5. The method according to claim 1, wherein the molecule specifically binding the analyte represents an anti-analyte antibody, an aptamer, a peptide, a nucleic acid or a chelator, which specifically binds the analyte.

6. The method according to claim 5, wherein the molecule specifically binding the analyte is an anti-analyte antibody or a fragment thereof.

7. The method according to claim 1, wherein the linker of the first conjugate comprises a water-soluble PEG linker molecule and the linker of the second conjugate comprises a water-soluble linker molecule.

8. The method according to claim 1, wherein the reagents are added in soluble form and an electrochemical detection of the binding is carried out in real time.

9. The method according to claim 1, wherein all the reagents are added to the sample as a ready-made mixture and an electrochemical detection of the binding is carried out in real time.

10. The method according to claim 1, wherein all the reagents are provided as dry reagents in a reaction vessel and only dissolved by addition of the sample and, optionally, a buffer, which marks a beginning of the analysis.

11. The method according to claim 1, wherein the immunoassay is performed in a microfluidic analysis system (lab-on-a-chip) and/or on a fully automated analyzer.

12. The method according to claim 1, wherein a structured electrode is used instead of a simple electrode for detection.

13. The method according to claim 1, wherein an enzymatically catalyzed cyclic reaction is employed instead of a simple electrochemical redox reaction.

14. The method according to claim 1, wherein the linker of the first conjugate and the linker of the second conjugate each comprise a water-soluble PEG linker molecule.

* * * * *